United States Patent
Tevs et al.

(10) Patent No.: US 9,693,496 B2
(45) Date of Patent: Jul. 4, 2017

(54) AGRICULTURAL PLANTING DEPTH SENSOR

(71) Applicant: Deere & Company, Moline, IL (US)

(72) Inventors: Nikolai R. Tevs, Daytona Beach Shores, FL (US); Jeffrey S. Puhalla, Hawley, MN (US); Elijah B. Garner, Bettendorf, IA (US); Michael L. Rhodes, Richfield, MN (US)

(73) Assignee: Deere & Company, Moline, IL (US)

( * ) Notice: Subject to any disclaimer, the term of this patent is extended or adjusted under 35 U.S.C. 154(b) by 36 days.

(21) Appl. No.: 14/871,254

(22) Filed: Sep. 30, 2015

(65) Prior Publication Data
US 2017/0086349 A1   Mar. 30, 2017

(51) Int. Cl.
| | | |
|---|---|---|
| *A01C 5/06* | (2006.01) | |
| *G01N 27/22* | (2006.01) | |
| *G06F 3/048* | (2013.01) | |
| *A01B 76/00* | (2006.01) | |

(52) U.S. Cl.
CPC .......... *A01C 5/064* (2013.01); *A01B 76/00* (2013.01); *G01N 27/22* (2013.01); *G06F 3/048* (2013.01)

(58) Field of Classification Search
CPC .. A01C 7/203; A01C 7/08; A01C 5/06; A01B 76/00
See application file for complete search history.

(56) References Cited

U.S. PATENT DOCUMENTS

| | | | |
|---|---|---|---|
| 4,413,685 A | | 11/1983 | Gremelspacher et al. |
| 5,653,292 A | * | 8/1997 | Ptacek .................... A01C 7/203 |
| | | | 172/239 |
| 6,085,846 A | | 7/2000 | Buchl et al. |
| 6,216,795 B1 | | 4/2001 | Buchl |
| 6,608,672 B1 | * | 8/2003 | Shibusawa ........... A01B 79/005 |
| | | | 250/339.11 |
| 8,204,689 B2 | | 6/2012 | Christy et al. |

(Continued)

FOREIGN PATENT DOCUMENTS

| | | |
|---|---|---|
| CA | 2313376 A1 | 1/2001 |
| WO | WO 2014/066654 A1 | 5/2014 |

*Primary Examiner* — John G Weiss
(74) *Attorney, Agent, or Firm* — Christopher J. Volkmann; Kelly, Holt & Christenson, PLLC

(57) ABSTRACT

An agricultural planting machine is described. In one example, the machine comprises a trench opener configured to open a trench, and a trench depth sensing system comprising a ground-engaging component and a trench depth sensor configured to generate a signal indicative a displacement of the ground-engaging component by directly sensing a surface of the ground engaging component. In one example, an agricultural planting machine comprising a trench opener configured to open a trench, and a trench depth sensing system comprising a ground-engaging component and a capacitive sensor comprising a transmitter element driven by an input signal to generate an electric field and a receiver element configured to generate an output signal based on a capacitive coupling between the transmitter and receiver elements, wherein the capacitive coupling changes based on movement of the ground-engaging component within the electric field. A trench depth calculation component is configured to generate an indication of trench depth based on the output signal.

20 Claims, 12 Drawing Sheets

(56) References Cited

U.S. PATENT DOCUMENTS

| | | | |
|---|---|---|---|
| 8,909,436 B2* | 12/2014 | Achen | A01C 5/062 |
| | | | 111/134 |
| 2014/0303854 A1 | 10/2014 | Zielke | |
| 2015/0094917 A1* | 4/2015 | Blomme | A01C 21/005 |
| | | | 701/50 |
| 2015/0230391 A1* | 8/2015 | Houck | A01C 7/203 |
| | | | 701/50 |
| 2015/0264857 A1* | 9/2015 | Achen | A01B 49/06 |
| | | | 111/149 |
| 2015/0289438 A1* | 10/2015 | Sauder | A01B 79/005 |
| | | | 701/50 |
| 2016/0037709 A1* | 2/2016 | Sauder | A01C 7/203 |
| | | | 700/275 |
| 2016/0338260 A1* | 11/2016 | Hahn | A01C 5/062 |

\* cited by examiner

AGRICULTURAL PLANTING DEPTH SENSOR

FIELD OF THE DESCRIPTION

The present description generally relates to sensors and, more particularly, but not by limitation, to sensors on an agricultural machine for sensing trench or planting depth.

BACKGROUND

One example agricultural machine is a planting machine that includes row units configured to plant seeds in a plurality of rows. Examples of planting machines include, but are not limited to, box drills, air seeders, and row crop planters. To maximize yield, the seeds are planted in furrows or trenches with proper depth based on various features such as crop type and soil conditions. In one example, row units can be configured to push a blade, disk, or other trench opener through the soil to create a trench for seeds to be placed in. Row units can also be configured to utilize a closing mechanism that follows the openers and pushes soil back into the opening, thereby filling the trench and covering the seeds.

In addition to planting seeds for crops, such as corn, soybeans, sunflowers, and sugar beets, these example planting machines can be similarly used to evenly distribute other agricultural material such as fertilizers and herbicides. Attaining proper depth and monitoring depth variation can be important to crop yield.

The discussion above is merely provided for general background information and is not intended to be used as an aid in determining the scope of the claimed subject matter.

SUMMARY

An agricultural planting machine is described. In one example, the machine comprises a trench opener configured to open a trench, and a trench depth sensing system comprising a ground-engaging component and a trench depth sensor configured to generate a signal indicative a displacement of the ground-engaging component by directly sensing a surface of the ground engaging component. In one example, an agricultural planting machine comprising a trench opener configured to open a trench, and a trench depth sensing system comprising a ground-engaging component and a capacitive sensor comprising a transmitter element driven by an input signal to generate an electric field and a receiver element configured to generate an output signal based on a capacitive coupling between the transmitter and receiver elements, wherein the capacitive coupling changes based on movement of the ground-engaging component within the electric field. A trench depth calculation component is configured to generate an indication of trench depth based on the output signal.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

Figure 1:
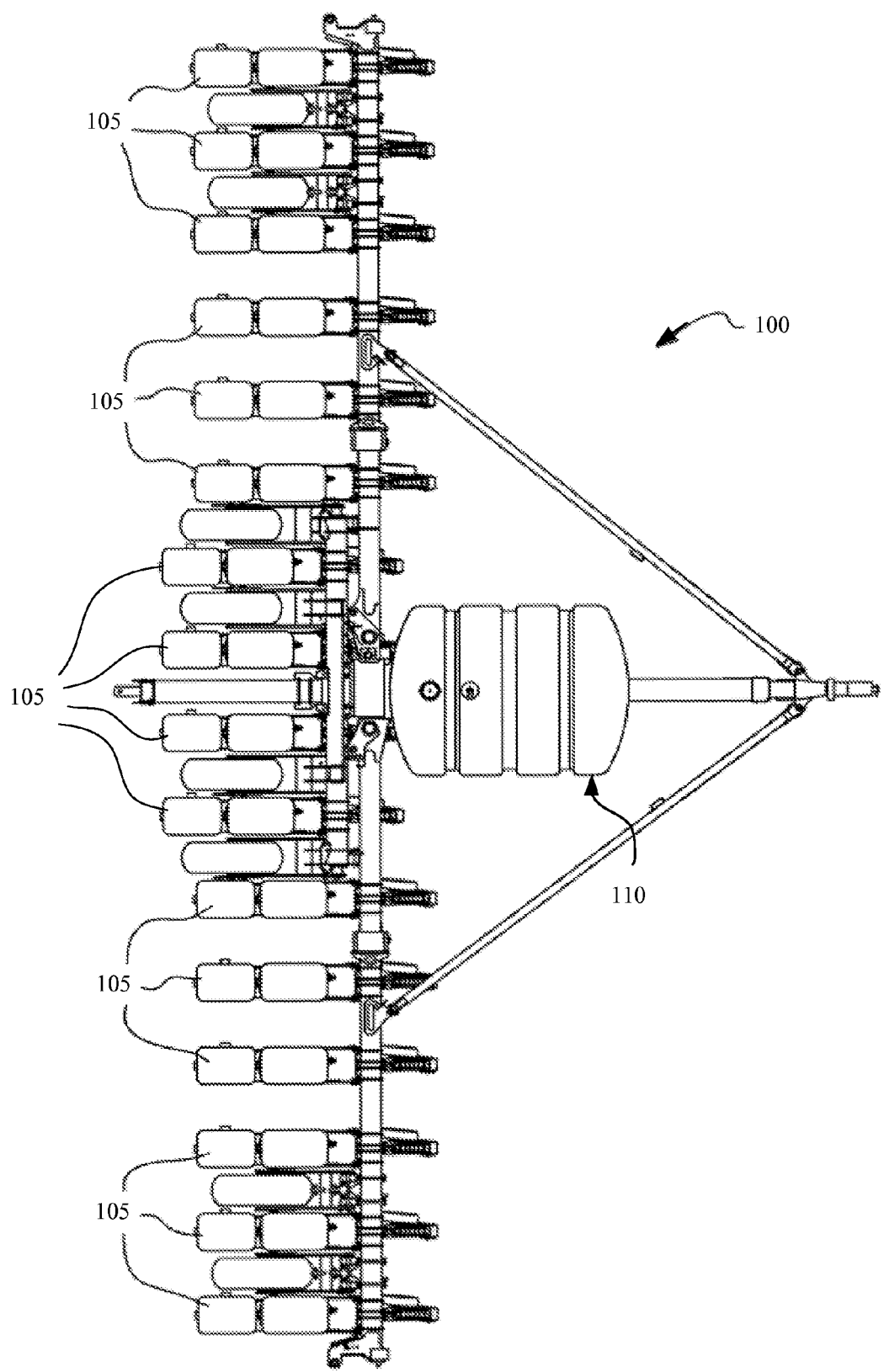
FIG. 1 illustrates one example of an agricultural planting machine that includes row units configured to plant seeds in a plurality of rows.

FIG. 1 illustrates one example of an agricultural planting machine 100 that includes row units configured to plant seeds in a plurality of rows. Machine 100 can comprise any of a variety of types of planting machine including, but not limited to, a box drill, an air seeder, and a row crop planter.

Agricultural planting machine 100 illustratively comprises a plurality of row units 105 and one or more product sources 110 (illustrative a product tank). Each product source 110 is configured to supply row units 105 with an agricultural product, such as, but not limited to, particulate material in the form of seed and/or fertilizer. In one example, separate seed and fertilizer sources are utilized to supply separate flows of seed and fertilizer to row units 105.

Alternatively, or in addition, each row unit 105 can have a separate product tank that holds agricultural product for the row unit. For example, a distribution system can be utilized to supply product for product source 110 to individual tanks at each row unit. Then, each row unit meters the product for the respective tank.

Row units 105 can comprise a variety of mechanisms for dispersing agricultural material to the ground, including one or more ground-engaging components. Examples of ground-engaging components include a trench opener or other component(s) for forming a trench or furrow in the soil, a ground-engaging seed firmer, and/or ground-engaging components utilized in a trench depth sensing system. One advantage to utilizing a plurality of row planting units is that planting machine 100 can consistently disperse the material in multiple rows as the machine makes a single pass across a field. Thus, row units are typically identical across a given planting machine, but need not be identical.

It is noted that while FIG. 1 illustrates agricultural planting machine 100 in the form of a row crop planter, in another example planting machine 100 can comprise an air seeder or a box drill. In an air seeder example, an air cart is pulled in front of or behind an implement having a plurality of transversely spaced row units. The air cart has product tank(s) and utilizes a pneumatic distribution system to pneumatically distribute the product to the row units.

Figure 2:
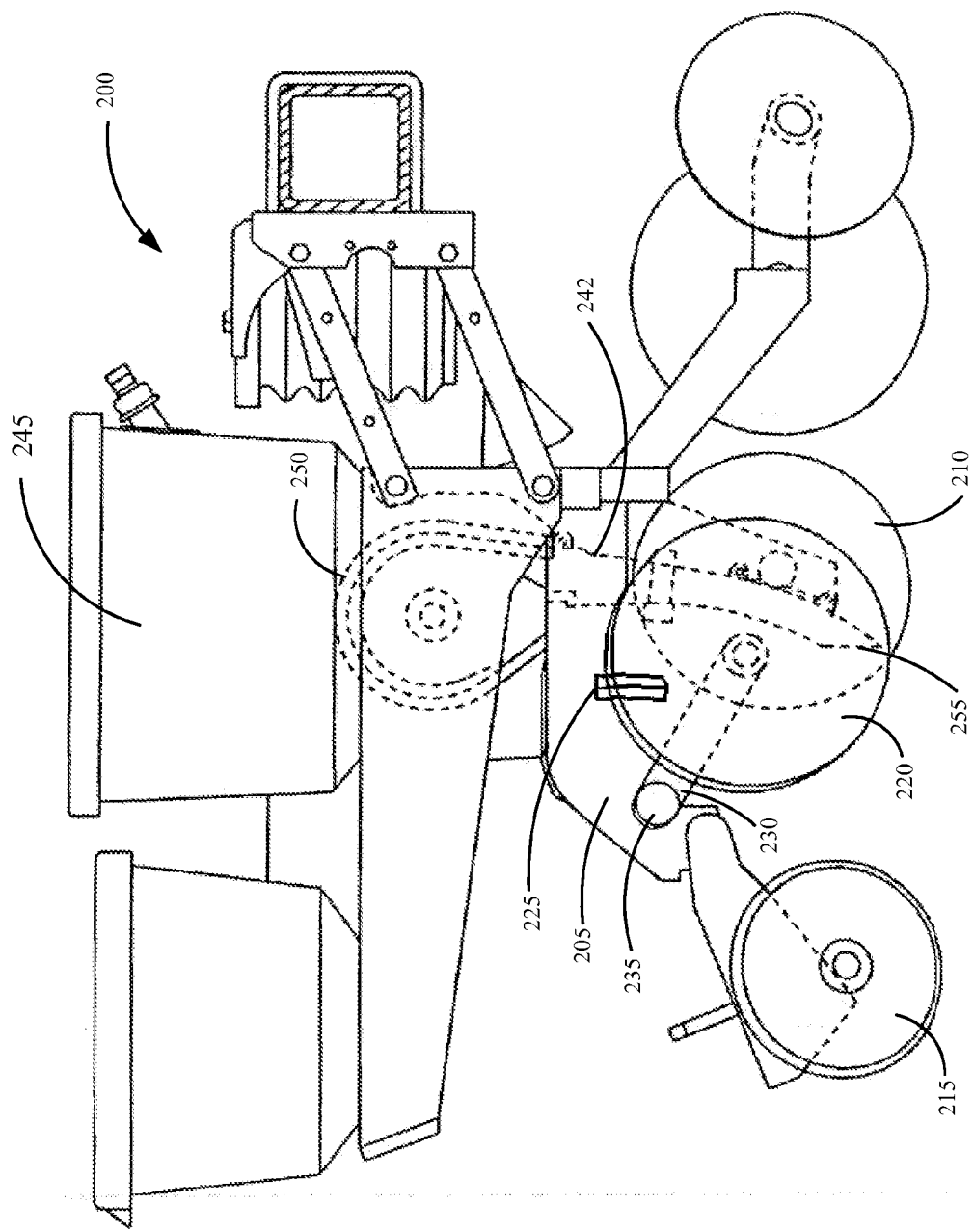
FIG. 2 illustrates one example of a row unit for an agricultural planting machine.

One example of a row unit 200 is shown in more detail in FIG. 2. It is noted that some or all components of row unit 200 can be utilized in a variety of different types of planting machines, including, but not limited to, box drills, air seeders, and row crop planters.

As shown in FIG. 2, example row unit 200 comprise a frame 205, a ground-engaging trench opener 210, a ground-engaging trench closer 215, a ground-engaging trench depth component 220, a pivot arm 230, a pivot arm connection 235, a material conveyance mechanism 242, and a material source 245.

Trench opener 210 comprises one or more components configured to form or open a trench, or furrow, in the soil for placement of agricultural material (e.g., seed and/or fertilizer) by conveyance mechanism 242. In one example, trench opener 210 comprises a blade or blade-like mechanism to form the trench. In the illustrated example, trench opener 210 comprises one or more disks. Conveyance mechanism 242 comprises, in one example, a gravity drop tube from a metering assembly, generally represented at reference numeral 250. Metering assembly 250 meters the material from material source 250 in a desired manner (e.g., singulating seed with a desired spacing).

Trench depth component 220 is configured to engage and follow a top of the soil alongside the trench formed by opener 210. In this manner, trench depth component 220 is utilized by a trench depth sensing system to determine a depth of the trench (e.g., by comparing the position opener 210 forming the trench and component 220 which is generally at the top of the trench). Component 220 can be of any of a variety of types of ground-engaging component(s). For example, component 220 can comprise a ground-engaging paddle, brush, fingers, or the like, that engage and traverse along the top of the soil. It is noted that while component 220 is illustrated as traversing the soil alongside the trench, in one example component 220 can be configured to traverse within the trench before or after placement of seed therein.

In the illustrated example, component 220 comprises a rotatable gauge wheel (also referred to as gauge wheel 220). Gauge wheel 220 can comprise any of a variety of materials, such as, but not limited to, plastic, rubber, and/or metal. In one example, gauge wheel 220 comprises a single material forming a unitary body (e.g., one piece of plastic, rubber, metal, etc.). In another example, gauge wheel 220 comprises a tire mounted on a wheel rim. The tire and rim can each be formed of any suitable material. For example, a solid plastic or rubber tire is mounted on a wheel rim. In another example, an inflatable tire is mounted on the wheel rim.

Figure 3:
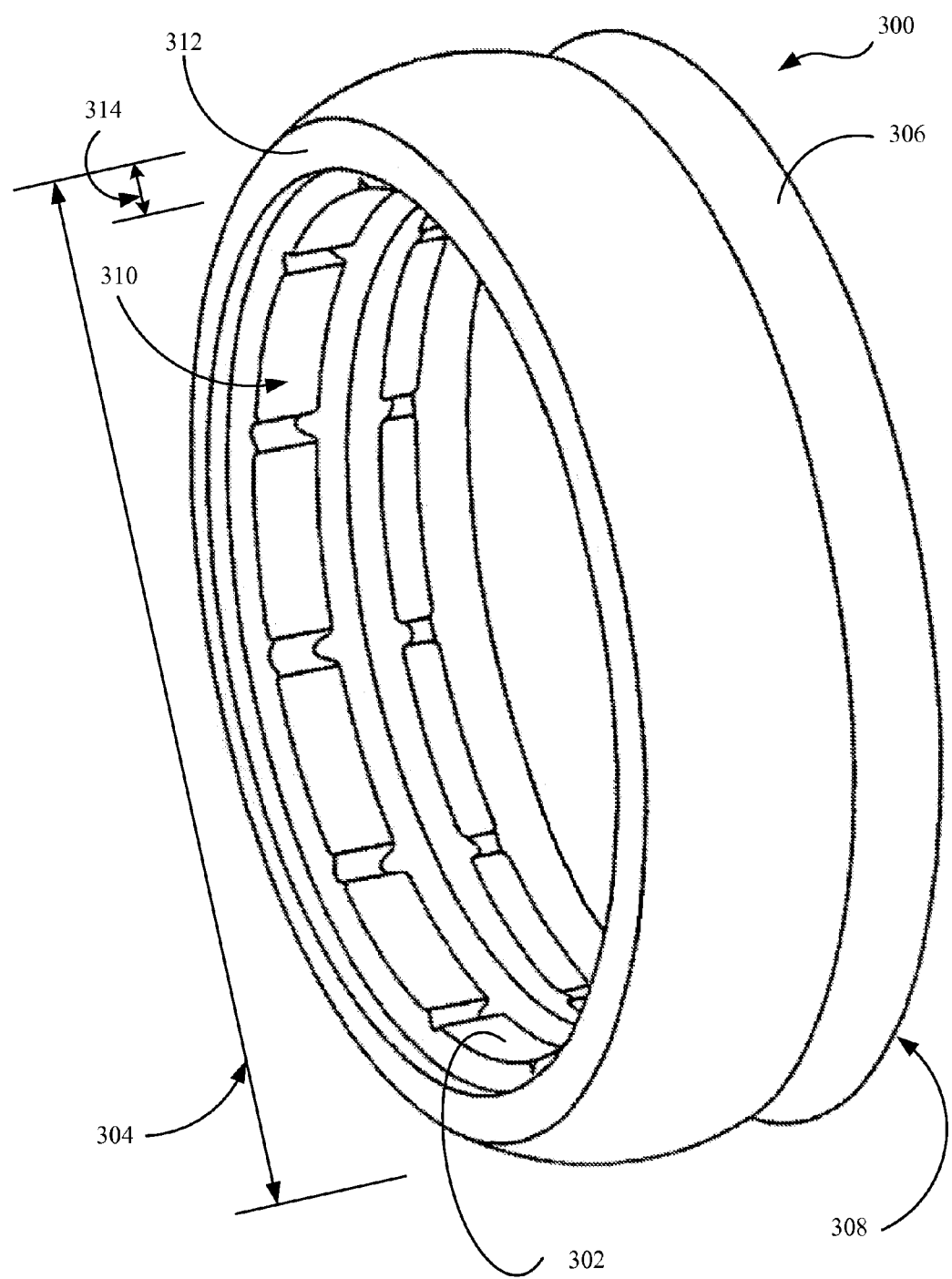
FIG. 3 illustrates one example of a gauge wheel.

FIG. 3 illustrates one example of a gauge wheel 300. Gauge wheel 300 is illustratively formed of a unitary body 302 (e.g., single piece of plastic or rubber). Body 302 has a diameter 304 and a ground-engaging surface 306. In the illustrated example, a first side 308 of body 302 is generally closed (with the exception of mounting holes) and a second side 310 has an opening 310 forming a lip 312 around the perimeter. Lip 312 has a width 314.

Referring again to FIG. 2, gauge wheel 220 is coupled to row unit frame 205 by pivot arm 230. Pivot arm 230 pivots about connection 235 thereby allowing gauge wheel 220 to traverse a vertical plane. In one example, row unit 200 comprises a plurality of gauge wheels 220. For instance, a first gauge wheel travels along a first side of the trench and a second gauge wheel travels along a second, opposite side of the trench. In this manner, when row unit 200 moves across an uneven surface, such as the slope of a hill or a bump in the terrain, the gauge wheels are located at different positions relative to the frame. For example, one gauge wheel is on a downhill side of the trench and one gauge wheel is on an uphill side of the trench. An average of the two gauge wheel positions can be used for a trench depth determination.

In one example operation, row unit 200 is moved from a stored position to an operating position, in which row unit 200 is lowered to the ground. In one example, opener 210 is in a fixed position relative to frame 205. Thus, downforce can be applied to row unit 200 and effectively push trench opener 210 into the ground. In one example, this downforce is pneumatic. In another example, this downforce is applied by hydraulically-powered cylinders.

As row unit 200 moves forward during planting, opener(s) 210 create a trench by pushing the soil away from a center line. An opening 255 from conveyance mechanism 242 is located in or over the trench to deposit the material in the trench. In one example, opening 255 is formed by a separate seed boot, or other mechanism, that is positioned alongside or behind opener 210. In another example, opening 255 is formed in or on opener 210. For example, a blade opener can have an opening that deposits the material in the trench formed by the blade opener. Trench closer 215 follows opener 210 to push soil back into the trench, thereby covering the material placed in the trench.

The trench or planting depth can vary based on the mount of downforce applied to opener 210 and/or the soil conditions. In some scenarios, the soil type, soil conditions (e.g., moisture, etc.), and/or residue can vary significantly within different sections of the field, which can result in significant trench depth variation without adjustments to the downforce. In any case, gauge wheel 220 generally follows the top of the terrain, and can be utilized to make those adjustments to maintain a relatively constant, proper planting depth to encourage optimal yields. For instance, shallow planting can delay germination if the soil is too dry and deep planting can also delay germination if the soil temperature is too low.

An example system for sensing trench depth utilizes a sensor at pivot arm connection 235, to sense an angle of pivot arm 230. In other words, knowing the length of pivot arm 230 and a diameter of gauge wheel 220, the pivot arm angle can give a general indication of the bottom, ground engaging surface of wheel 220. In one example, a Hall Effect or other magnetic sensor is utilized at connection 235. However, such a sensor system can be highly susceptible to adverse effects due to ambient condition changes, and metal parts on the row unit can affect the magnetic field, resulting in inaccurate depth sensing. Further, terrain material (e.g., soil, crop residue, other debris etc.) can build up on the gauge wheel, thereby causing the gauge to elevate away from the top of the trench as the effective diameter of the gauge wheel is increased. This results in the sensing system indicating a deeper trench than what is actual formed. Further, because the sensor is disposed at the pivot point, away from the gauge wheel, any inaccuracies in the sensed arm angle amplify the gauge wheel position error.

The present disclosure describes a trench depth sensing system that, in illustrated examples, includes a trench depth sensor positioned to directly sense a ground-engaging component, such as opener 210 and/or gauge wheel 220, to give an accurate indication of trench depth. In other words, the example trench depth sensor can be positioned to sense a surface of the ground-engaging component to provide an indication of the relative position. Examples of sensors that can be utilized include, but are not limited to, an optical sensor, a microwave sensor, an ultrasonic sensor, a radio frequency sensor, a micropower impulse radar, and the like. For instance, the sensor can be locate over gauge wheel 220 to indicate a displacement of gauge wheel 220 in a vertical direction relative to frame 205.

In one example, a capacitive or dielectric sensor is utilized. The capacitive sensor is configured to measure dielectric permittivity of an adjacent medium. Examples of a capacitive trench depth sensing system are discussed in further detail below. Briefly, however, in one example a capacitive sensor comprises a set of sensing elements, each configured to generate a signal that is indicative of dielectric properties of a medium proximate the sensing element. Each sensing element can therefore distinguish between surfaces or other mediums with different dielectric properties, such as plastic, rubber, metal, air, water, soil, etc.

With respect to the example of FIG. 3, a capacitive trench depth sensor 225 can be disposed on frame 205 and configured to sense a surface position of gauge wheel 220. Distinguishing between surface properties, the sensor can effectively determine the displacement of gauge wheel 220, taking into account any debris build-up on the perimeter of wheel 220. This can provide accurate gauge wheel height measurements, and allow for more precise row unit adjustments to attain proper planting depth.

It is noted that while examples illustrated herein describe a capacitive sensor sensing gauge wheel position, the capacitive sensor can sense trench depth in other ways as well. In one example, the capacitive sensor can sense other ground engaging components, such as the trench opener and/or other types of gauge components (e.g., non-wheels, a paddle, etc.). In one example, the capacitive sensor can be positioned to directly sense the depth of the trench. For instance, the capacitive sensor can be placed on the trench opener to detect the depth of the furrow by measuring a height of a seed furrow sidewall. In this example, rather than placement on a non-rigid element, such as a seed firmer, which can give inaccurate measurements due to its flexibility, the capacitive sensor is mounted rigidly with respect to the frame. That is, with respect to the example of FIG. 2, the opener is fixedly coupled to the frame, to which a downforce is applied to set a trench depth.

Figure 4:
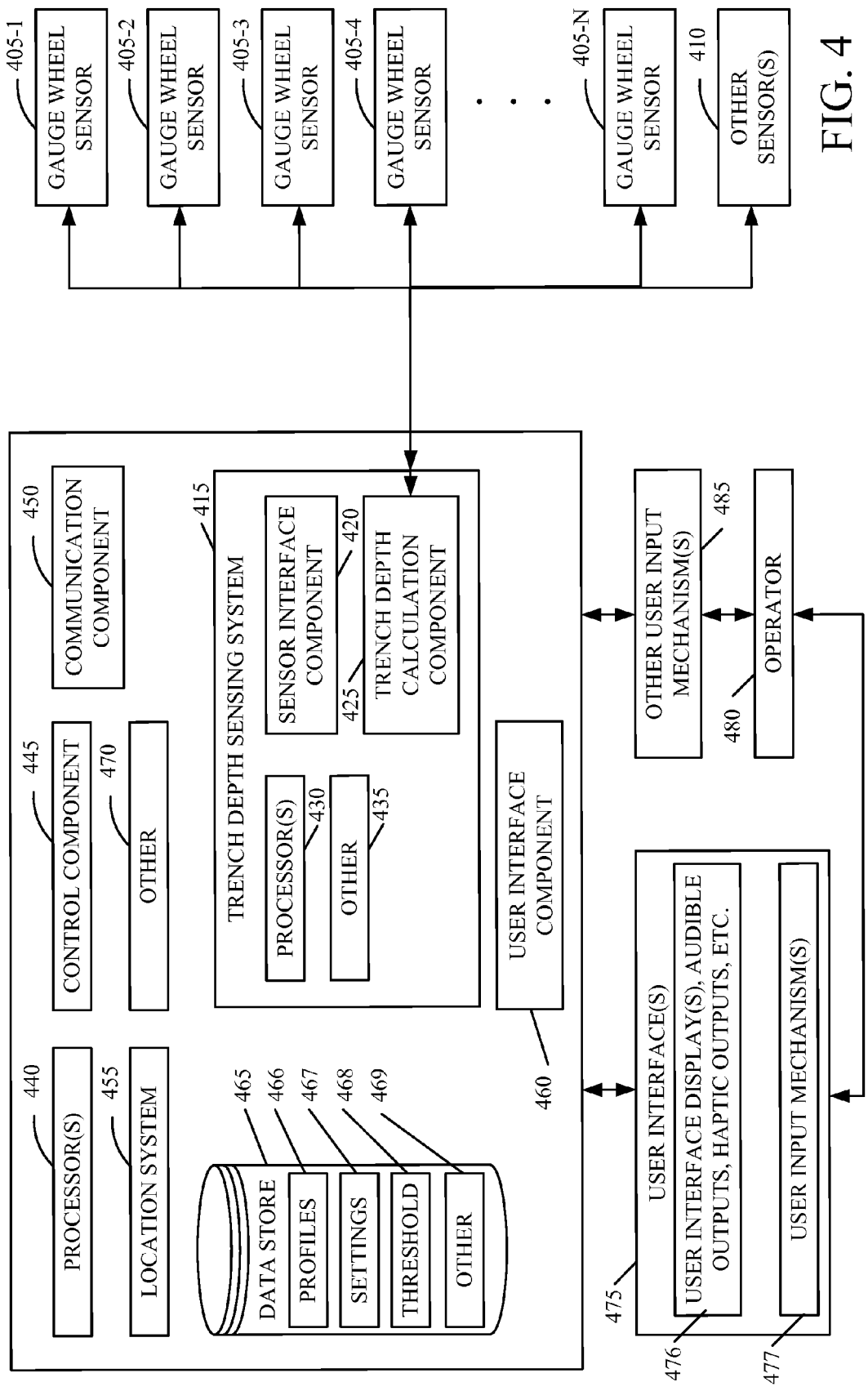
FIG. 4 is a schematic diagram of one example of a planting depth monitoring and control system.

FIG. 4 is a schematic diagram of one example of a planting depth monitoring and control system 400. In one example, system 400 is utilized on a planting machine, such as, but not limited to, any of the planting machines discussed above.

System 400 comprises a plurality of gauge wheel sensors 405-1, 405-2, 405-3, 405-4, and 405-N (collectively or individually referred to as gauge wheel sensors 405). Each sensor 405 is configured to sense the position of a gauge wheel. In one example, multiple gauge wheel sensors 405 sense a same gauge wheel. Further, as mentioned above, a particular row unit can have multiple gauge wheels, and thus multiple sensors 405. System 400 can have other sensors 410, as well.

A trench depth sensing system 415 includes a sensor interface component 420, a trench depth calculation component 425, one or more processors 430, and can include other components 435 as well. Sensor interface component 420 is configured to interface with sensors 405 to send and receive signals therewith.

System 400 illustratively includes one or more other processors 440, a control component 445, a communication component 450, a location system 455, a user interface component 460, a data store 465, and can include other components 470 as well. Data store can store operator profiles 466, machine settings 467 and/or thresholds 468, and can store other items 469 as well. The data in data store 465 can be utilized during a planting operation to control the machine operation (e.g., speed, planting depth, etc.). Further, data store 465 can store information regarding the planting operation, such as geo-referenced planting depth information. For example, location system 455 (e.g., a GPS receiver, dead-reckoning system, etc.) obtains a location of the machine during planting and stores the location information along with the corresponding planting depth information, indicating a planting depth at the location.

User interface component 460 is configured to generate one or more user interfaces 475 for an operator 480. This can include both input and output mechanisms. For instance, as illustrated in FIG. 4 one or more user interface displays, audible outputs, haptic outputs, and the like (represented by block 476) can be rendered to the user. Alternatively, or in addition, user interfaces 475 can include user input mechanism(s) 477. Other user input mechanism(s) 485 can be provided as well.

Using interface component 420, system 415 is configured to receive an electrical signal from each sensor 405 indicative of a gauge wheel position. Based on the signals, trench depth calculation component 425 calculates trench depth based on a different between the position of a trench opener (not shown in FIG. 4) and the corresponding gauge wheel(s). For example, when the sensor 405 is mounted on the row unit frame, component 425 can utilize the mounting position as a reference point in calculating the trench depth.

Trench depth sensing system 415 can provide the signals received from sensors 405 and/or information processed by system 415 based on the sensor signals, to other component(s) in system 400. For example, system 415 can communicate with control component 445, which is configured to control (e.g., automatically or based on operator input) other machine system(s). For instance, component 445 can control one or more electrical systems, mechanical systems, hydraulic systems, pneumatic systems, air over hydraulic systems, or other systems to control downforce, seed dispersal, and/or other operations in response to the calculated trench depth. In one example, control component 445 can control the depth of trench openers by generating control signals to increase or decrease the downforce applied to a row unit.

In one example, user interface(s) 475 provide output to operator 480 that indicate trench or planting depth, as determined by trench depth sensing system 415. Operator 480 can interact with user input mechanism(s) 477 and/or 480 to control various components of system 400, or other system(s) of the machine, based on this output. For example, operator 480 can adjust machine speed and/or the downforce on the row units to change the trench depth. The user input mechanisms can include, for example, touch screen gestures, or other input configurations such as switches, levers, push buttons, keypads, pedals, joysticks, etc.

As mentioned above, sensors 405 can comprise any of a variety of sensor types. In the following illustrated examples, however, sensors 405 comprise capacitive sensors configured to generate an electrical output signal representative of gauge wheel position. For sake of illustration, but not by limitation, system 400 will now be described in conjunction with FIGS. 5 and 6.

Figure 5A:
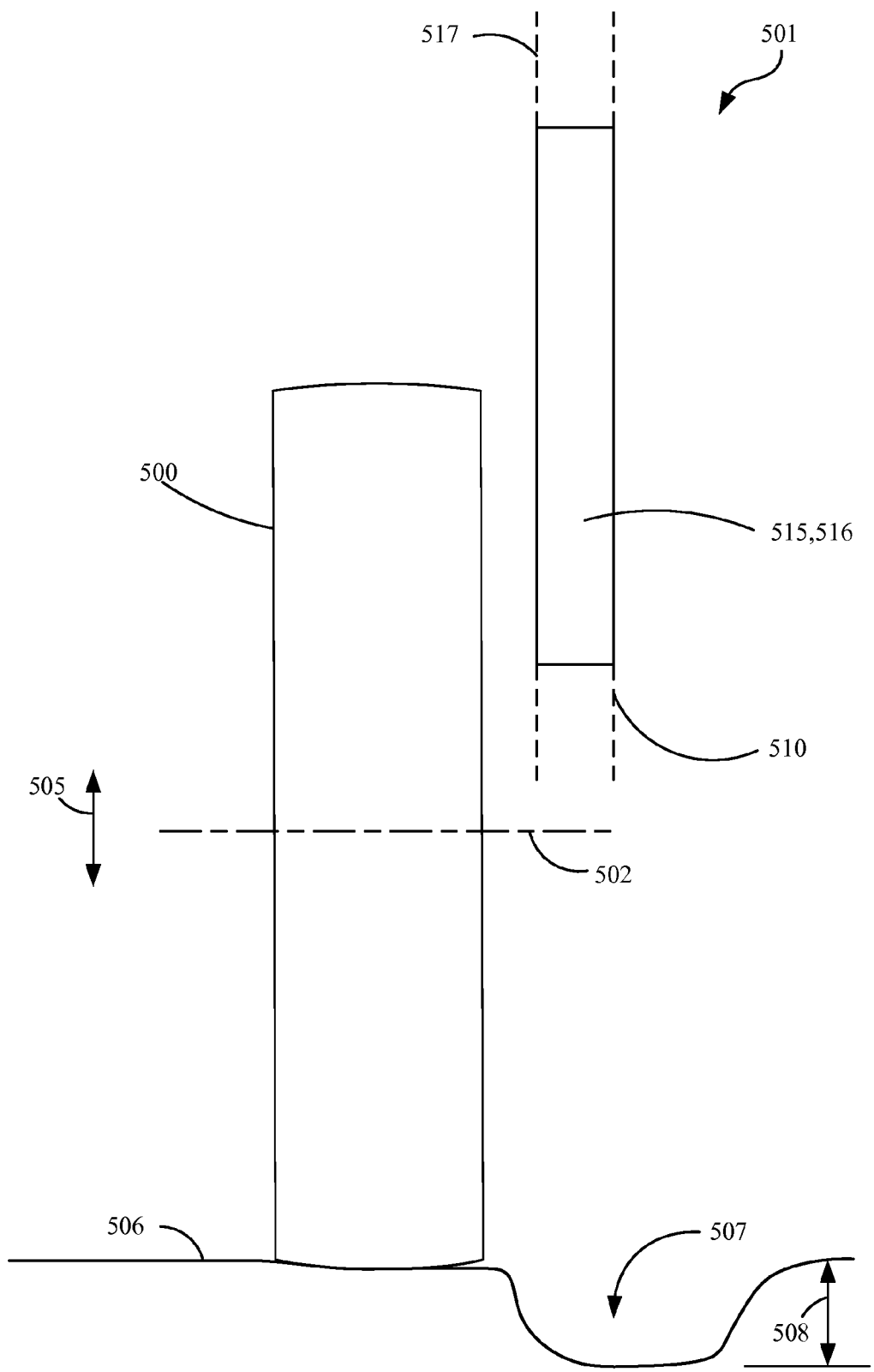
FIGS. 5A and 5B are simplified schematic views of a gauge wheel sensor disposed proximate a gauge wheel, in one example.
Figure 5B:
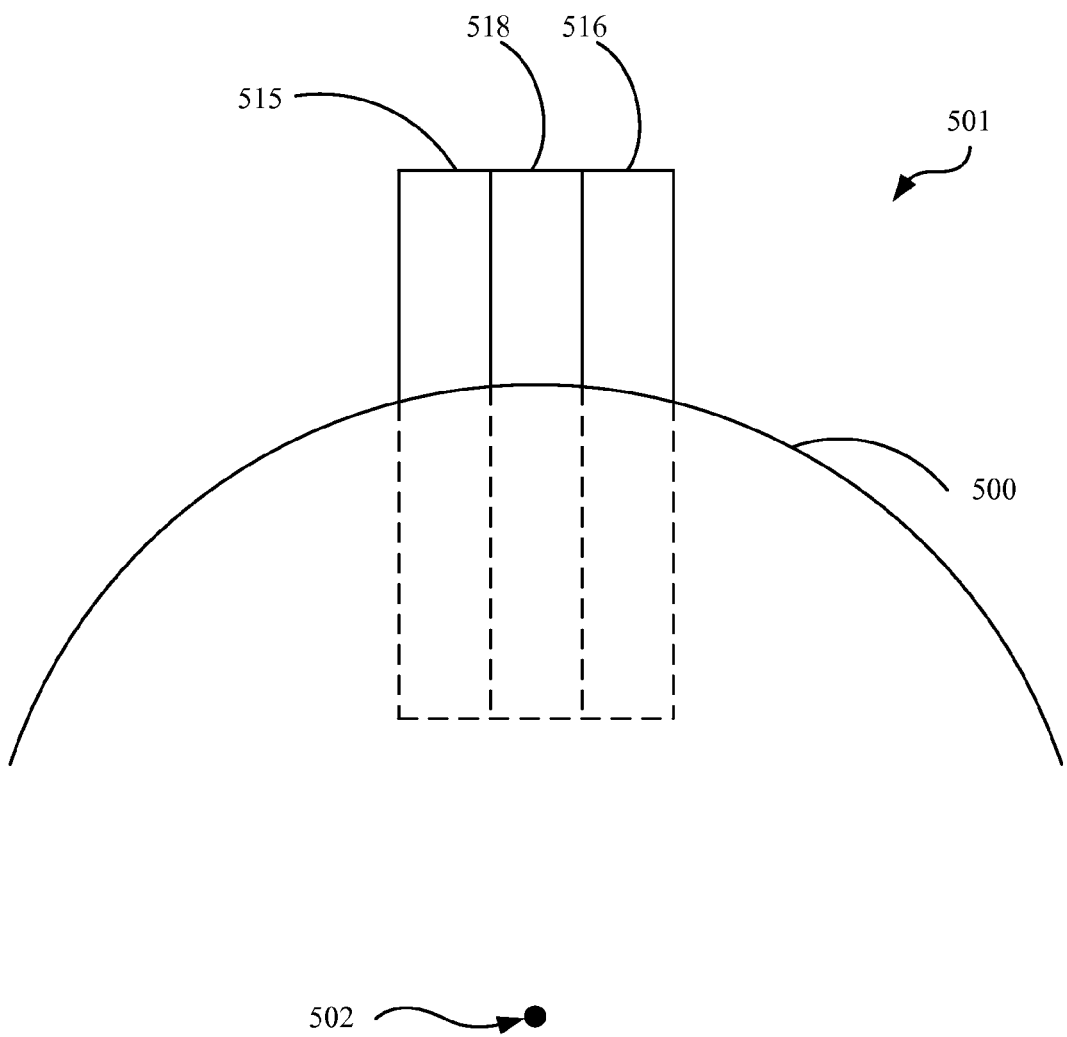

FIGS. 5A and 5B (collectively referred to as FIG. 5) are simplified schematic views of a gauge wheel sensor 501 disposed proximate a gauge wheel 500, in one example (FIG. 5A is perpendicular to wheel axis 502 and FIG. 5B is parallel to wheel axis 502). As shown in FIG. 5, sensor 501 is mounted on a row unit frame, generally represented by dashed line 510. Gauge wheel 500 is configured to move vertically (illustrated by double arrow 505) as gauge wheel 500 follows terrain 506 alongside a trench 507. Based on the fixed mounting position of sensor 501, the relative positions of the trench opener and gauge wheel 500 can be determined based on output signals generated by sensor 501. The depth 508 of trench 507 can be calculated from these relative positions.

Sensor 501 includes at least one transmitter element or electrode and at least one receiver element or electrode. As shown in FIG. 5, sensor 501 can comprise a pair of co-planar conductive plates (or other electrode elements) that face gauge wheel 500 (i.e., a first transmitter plate 515 and a second receiver plate 516) that are at fixed positions relative to one another. Plates 515 and 516 are aligned along a plane 517. The spacing between plates 515 and 516 is defined by an gap 518, which can include an insulator. An input signal is applied to transmitter plate 515 to generate an electric field. Based on the capacitance between plates 515 and 516, an output signal is generated by receiver plate 516. For sake of illustration, but not by limitation, the capacitance between two conductive plates of a similar profile can be expressed equation (1):

$$C = \epsilon_0 KA/d; \qquad \text{EQUATION (1)}$$

where C is the capacitance, $\epsilon_0$ is the permittivity of free space constant, K is the dielectric constant of material(s) in the electric field proximate the electrodes, A is the area of the plates, and d is the distance between the plates.

Since the area and profile of plates 515 and 516, and the distance between them, is fixed (and any temperature change is nominal), the output signal from plate 516 is only significantly affected by changes in the dielectric constant of any materials in the electric field. As such, knowing the dielectric properties of gauge wheel 500, a position of the gauge wheel relative to sensor 501 can be accurately determined. For example, in the case of using a single receiver element, the output signal can be used by trench depth calculation component 425 to determine how much of gauge wheel 500 is in front of sensor 501. This can then be used as an indication of a height of gauge wheel 500 relative to the row unit frame.

Figure 6A:
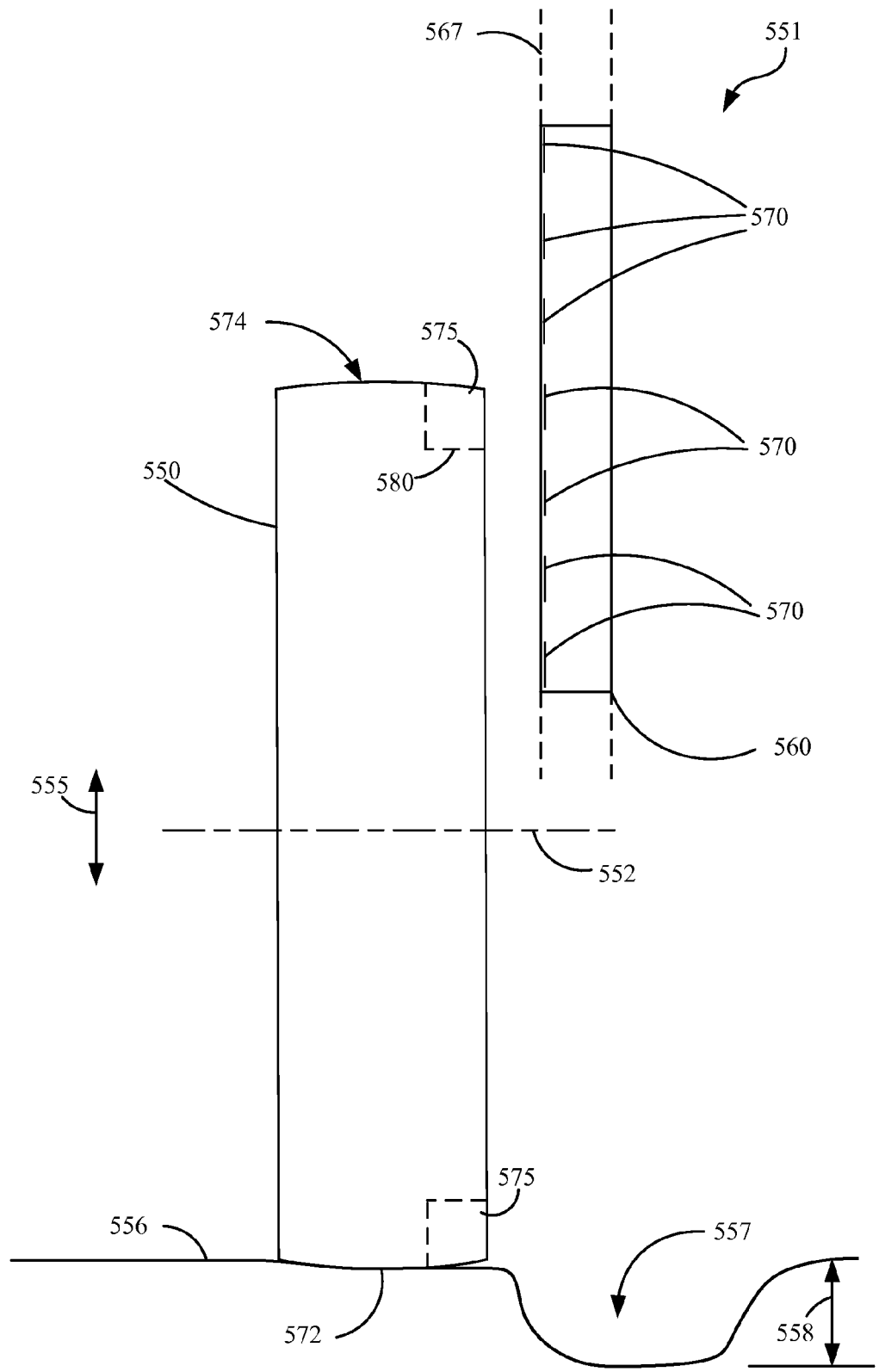
FIGS. 6A and 6B are simplified schematic views of a gauge wheel sensor disposed proximate a gauge wheel, in one example.
Figure 6B:
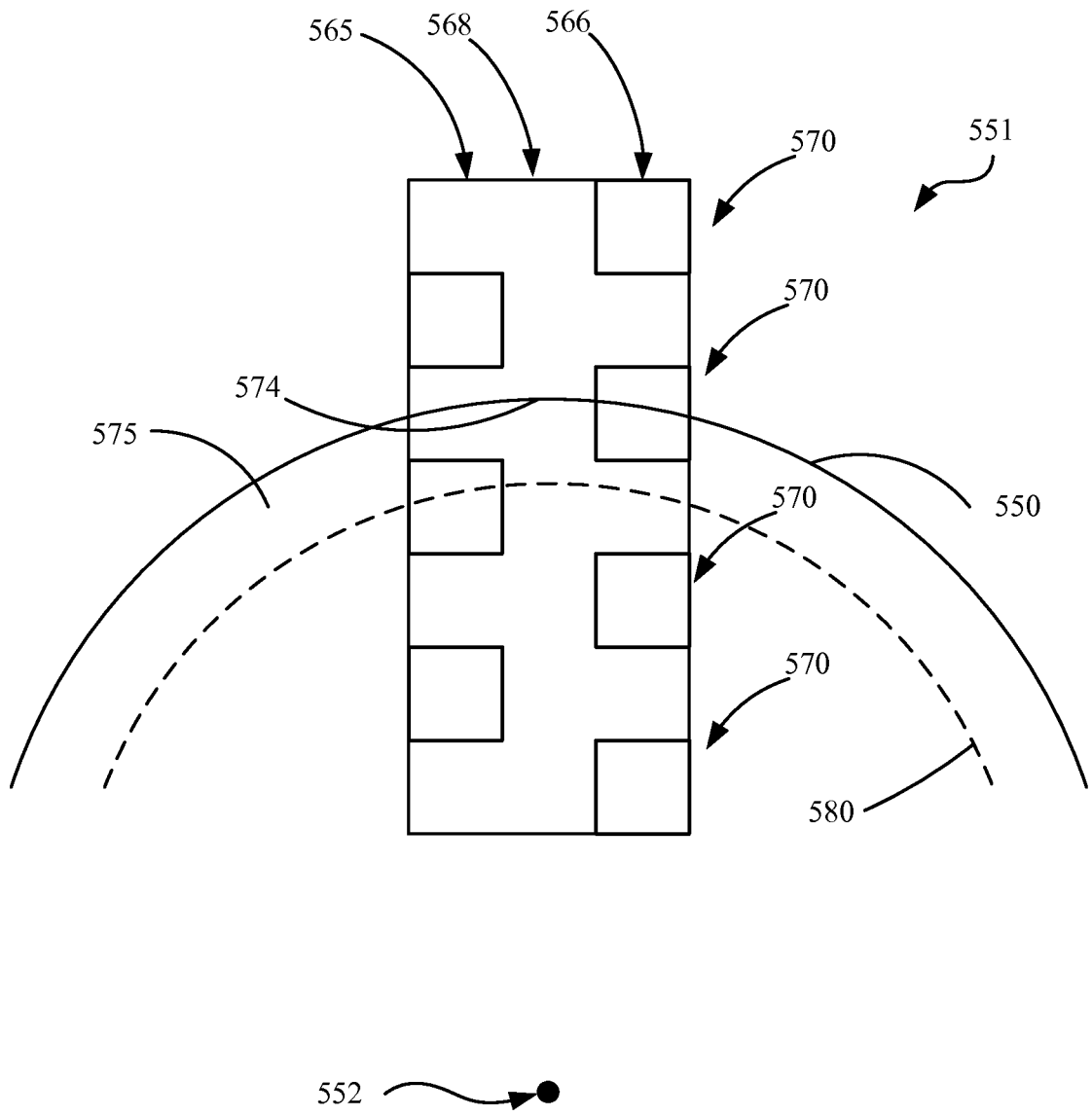

FIGS. 6A and 6B (collectively referred to as FIG. 6) are simplified schematic views of a gauge wheel sensor 551 disposed proximate a gauge wheel 550, in one example (FIG. 6A is perpendicular to wheel axis 552 and FIG. 6B is parallel to wheel axis 552). As shown in FIG. 6, sensor 551 is mounted on a row unit frame, generally represented by dashed line 560. Gauge wheel 550 is configured to move vertically (illustrated by double arrow 555) as gauge wheel 550 follows terrain 556 alongside a trench 557. Based on the fixed mounting position of sensor 551, the relative positions of the trench opener and gauge wheel 550 can be determined based on output signals generated by sensor 551. The depth 558 of trench 557 can be calculated from these relative positions.

Sensor 551 comprises an array of capacitive sensing elements 570 (generally represented in FIG. 6A by dashed lines). The array is formed by at least one transmitter element array 565 and at least one receiver element array 566 separated by a gap 568, which can include an insulator. Sensing elements 570 face gauge wheel 550 and are aligned along a plane 567. Each sensing element 570 is insulated from adjacent sensing elements and is configured to generate a signal based on capacitance across the sensing element 570, which is indicative of dielectric properties of a medium proximate the sensing element 570. In other words, the electrical output signal from each sensing element 570 is indicative of whether or not the sensing element 570 is adjacent gauge wheel 550. Further, in one example, based on the electrical output signal from a sensing element 550, system 415 can determine whether each sensing element 570 is adjacent debris (e.g., soil, crop residue, etc.) from terrain 556. This can indicate that dirt or other debris has built up on a surface of gauge wheel 550, which can be used in the trench depth calculation.

In the example of FIG. 6, each sensing element 570 comprises a receiver element or electrode in array 566 that generates an output signal in response to an electric field generated by at least one corresponding transmitter element or electrode in array 565, to which an input signal is applied. This signal is based on a capacitive coupling between the transmitter and receiver elements, which is effected by the dielectric properties of a material that is close to the elements.

To illustrate an example operation, a voltage (e.g., a radio frequency signal, etc.) is applied to transmitter element(s) in array 565, which emit an electric field in the adjacent environment. Depending on the dielectric properties of any objects or materials in the environment, especially in close proximity, receiver element(s) in array 566 generate an electrical signal which is indicative of, and can be used to determine, the dielectric properties of the materials, or lack of materials, in the environment.

As such, as gauge wheel 550 moves vertically, the electrical output signal of at least some of the sensing elements 570 will change, due to the dielectric properties of gauge wheel 550 and/or terrain debris on the gauge wheel 550. In one example, trench depth calculation component 425 performs a unit-less, differential measurement by comparing the signals from each sensing element 570 to determine the location of the top surface of terrain 556 relative to the row unit frame. For example, component 425 can normalize and then compare the signals from adjacent sensing elements 570 to identify which element(s) 570 indicate close presence of gauge wheel 550 and/or terrain debris, and which element(s) 570 do not indicate close presence of gauge wheel 550 (i.e., air only). In other words, component 425 can determine which element 570 is aligned with or closely proximate the top (represented by reference numeral 574 in FIG. 6) of gauge wheel 550. Based on this determination, and the known diameter of gauge wheel 550, component 425 can then identify a location of the bottom surface (represented by reference numeral 572 in FIG. 6) of gauge wheel 550. In one implementation, the displacement measurement error of sensor 551 is less than or equal to approximately one-tenth of an inch.

As mentioned above, in addition to the gauge wheel material, calculation component 425 can also identify the present of terrain debris (e.g., mud) on the top 574 of gauge wheel 550. For example, calculation component 425 can determine an approximate thickness of soil on wheel 550 based on which elements 570 indicate a dielectric property of mud, and then add the sensed debris thickness in calculating the location of the top of the terrain 556 relative to the reference location on frame 560.

In one example in which gauge wheel 550 includes a lip 575 (represented by dashed lines in FIG. 6), calculation component 425 can also identified the lower surface 580 of the lip 575, and utilized this information in calculating the displacement of gauge wheel. 550. For example, calculation component 425 can identify which sensing elements 570 indicate the lack of gauge wheel material below lip 575.

In one example, sensing elements 570 are placed on row unit frame 560 such that at least one sensing element remains above top 574 of gauge wheel 550 when the trench opener is at full depth (i.e., gauge wheel 550 is at a top of the vertical travel), and at least one sensing element remains below lower surface 580 when gauge wheel 550 is at a bottom of the vertical travel (i.e., the trench opener is at zero depth).

Figure 7:
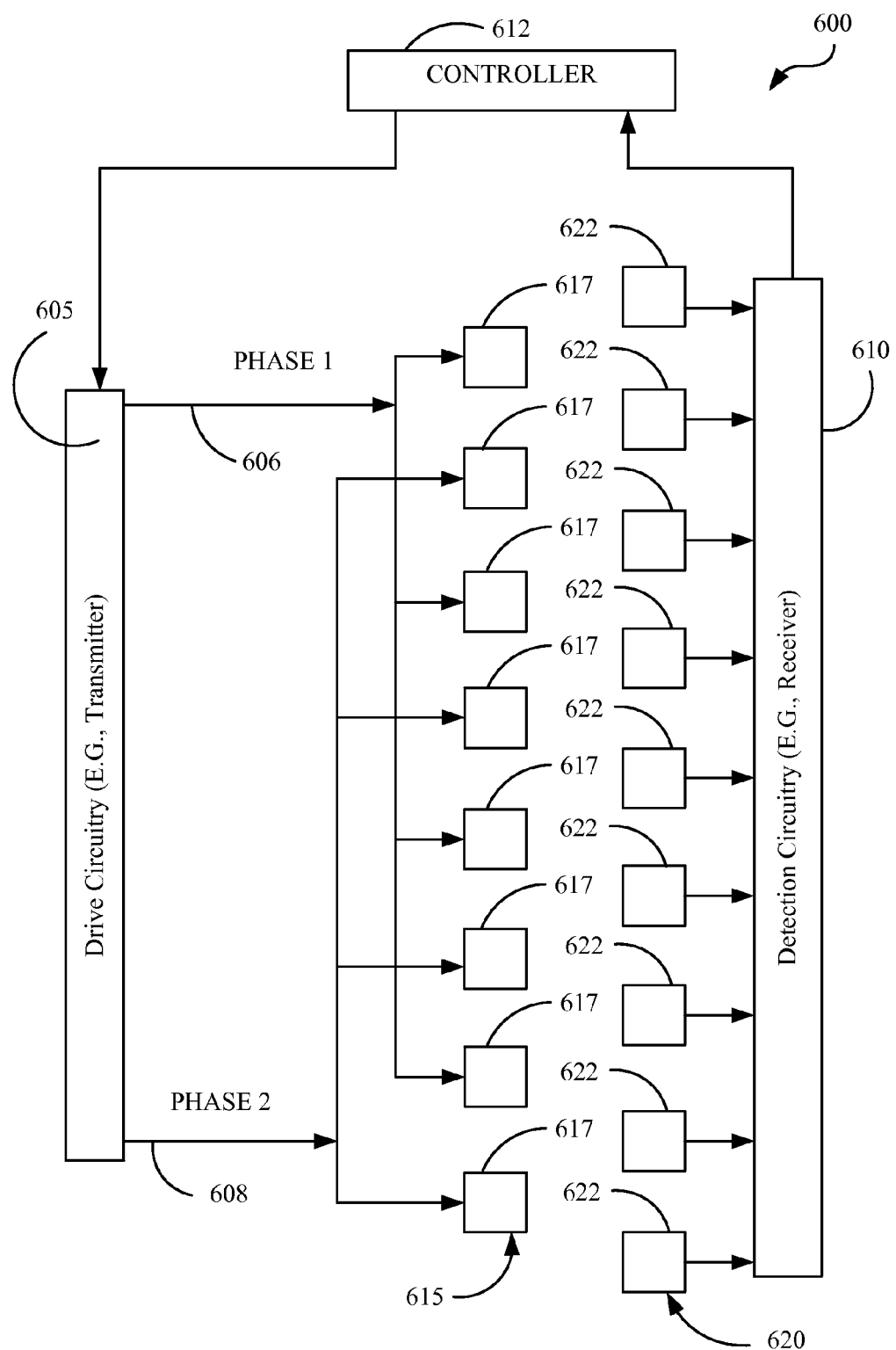
FIG. 7 is a block diagram of a sensor having an array of capacitive sensing elements, in one example.

FIG. 7 is a block diagram of one example of a capacitive sensor 600 having an array of capacitive sensing elements. Capacitive sensor 600 includes drive circuitry (e.g., a transmitter component) 605 coupled to a transmitter element array 615 and detection circuitry (e.g., a receiver component) 610 coupled to a receiver element array 620. Each of drive circuitry 605 and detection circuitry 610 are communicatively coupled to a controller 612. One example of controller 612 is sensor interface component 420 illustrated in FIG. 4.

Controller 612 is configured to apply a signal (e.g., an RF voltage, or other signal) to transmitter element array 615 through drive circuitry 605, and to detect a signal from receiver element array 620 through detection circuitry 610. The transmitter element array 615 and receiver element array 620 can be formed of any suitable material including, but not limited to, copper or other conductive material. In one example, arrays 615 and 620 are similar to arrays 565 and 566 shown in FIG. 6B.

Transmitter element array 615 comprises at least one array of transmitter elements 617 and receiver element array 620 comprises at least one array of receiver elements 622. The number of transmitter elements 617 and receiver elements 622 shown in FIG. 7 is by way of example only. Any number of elements can be utilized, for instance depending on the length of travel of a gauge wheel being sensed. Further, the elements can be spaced from one another by any suitable amount. In one example, array 615 and 620 are spaced from one another by at least approximately one-half inch, and the elements within each array 615,620 are spaced from one another by at least approximately one-quarter inch.

In the illustrated example, transmitter element array 615 comprises two transmitter element arrays that are separately driven by input signals. A first one of the transmitter element arrays is driven by a first input signal with a first phase (represented by line 606) and a second one of the transmitter element arrays is driven by a second input signal with a second phase (represented by line 608). The first and second phases are different, and can be offset by any desired amount (e.g., one hundred eighty degrees, etc.).

In the illustrated example, each transmitter element 617 is placed between two receiver elements, and is excited by an RF voltage (or other voltage). Each receiver element 622 is placed between a first transmitter element 617 excited by the first input signal phase and a second transmitter element 617 excited by the second input signal phase.

To determine gauge wheel displacement, drive circuitry 605 applies a voltage to transmitter array 615 to produce an electric field in the surrounding environment. A material surface (e.g., the gauge wheel, soil on the gauge wheel) proximate one or more of the sensing elements alters the charge on the corresponding receiver element(s) 622, based on the material's dielectric properties. The dielectric coupling between transmitter array 615 and receiver array 620 is used as an indication of object presence, and the type of object, proximate the sensing element. By comparing or otherwise analyzing the signals from each receiver element, the position of the gauge wheel can be determined.

Figure 8A:
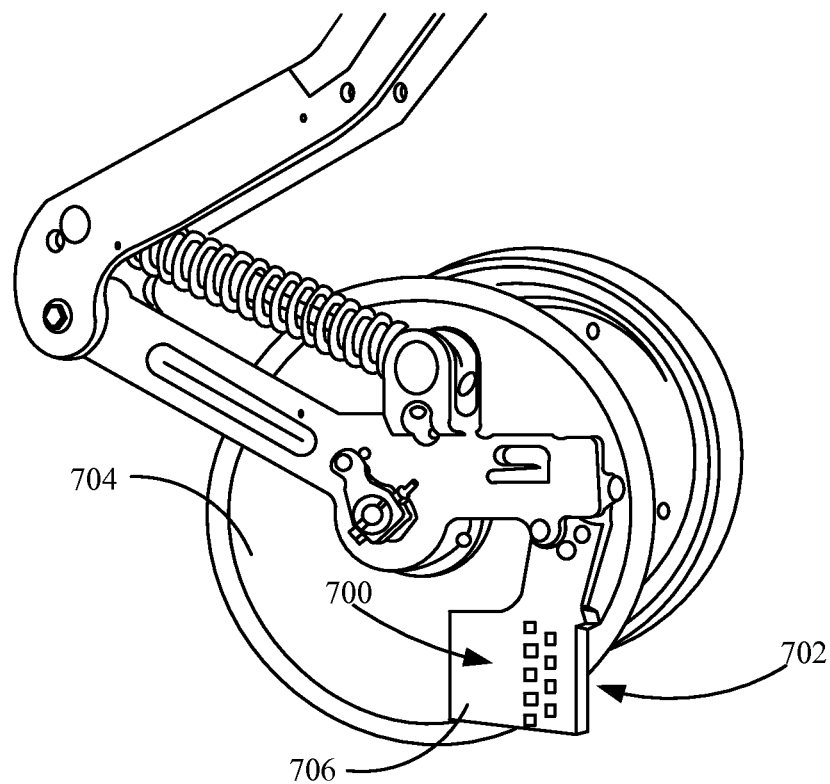
FIGS. 8A and 8B illustrate a capacitive sensor mounted on a trench opener, in one example.
Figure 8B:
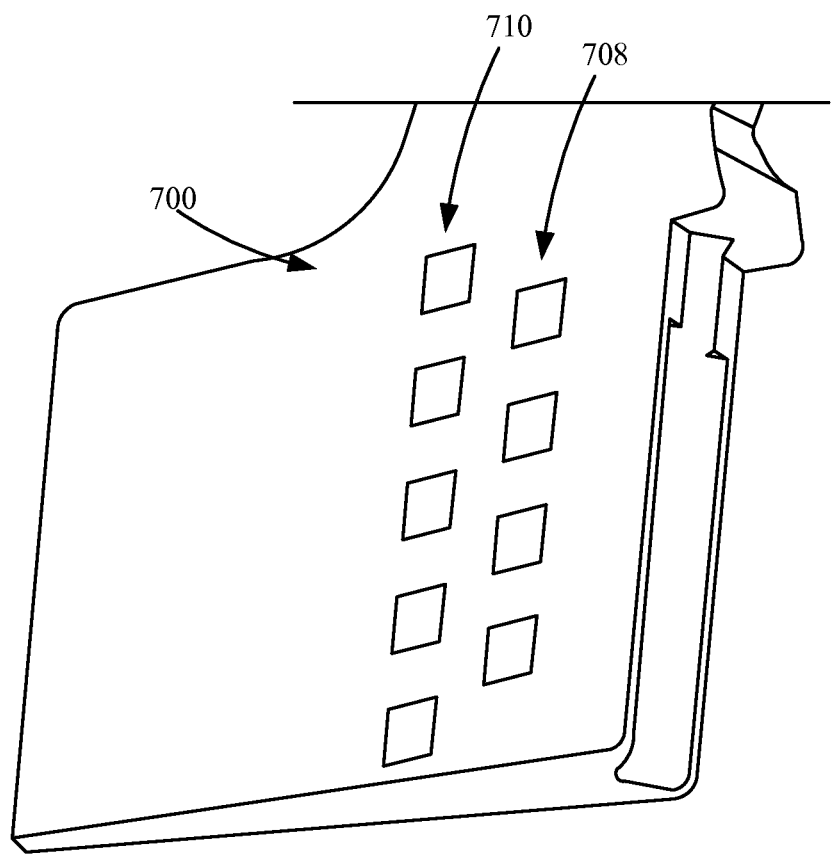

FIGS. 8A and 8B (collectively referred to as FIG. 8) illustrate a capacitive sensor 700 mounted on a trench opener 702, in one example. Trench opener 702 comprises a disk 704 and a wedge component 706 configured to open a seed trench. Capacitive sensor 700 includes a sensing element array, comprising at least one array of transmitter elements 708 and at least one array of receiver elements 710. In one example, the transmitter elements 708 and receiver elements 710 are substantially similar to transmitter elements 617 and receiver elements 622, respectively, illustrated in FIG. 7.

Capacitive sensor 700 is mounted on trench opener 702, and each sensing element comprises at least one transmitter element 708 driven by an input signal to generate an electric field and at least one receiver element 710 configured to generate an output signal indicative of dielectric properties of a medium proximate the sensing element. In the illustrated example, a trench depth is determine based on whether each capacitive sensing element is adjacent a sidewall of the trench based on the dielectric properties indicated by the output signal generated by the capacitive sensing element.

The present discussion has mentioned processors. In one example, a processor includes a computer processor with associated memory and timing circuitry, not separately shown. It is a functional part of the systems or devices to which they belong and are activated by, and facilitate the functionality of the other components or items in those systems.

Also, a number of user interface displays have been discussed. They can take a wide variety of different forms and can have a wide variety of different user actuatable input mechanisms disposed thereon. For instance, the user actuatable input mechanisms can be text boxes, check boxes, icons, links, drop-down menus, search boxes, etc. They can also be actuated in a wide variety of different ways. For instance, they can be actuated using a point and click device (such as a track ball or mouse). They can be actuated using hardware buttons, switches, a joystick or keyboard, thumb switches or thumb pads, etc. They can also be actuated using a virtual keyboard or other virtual actuators. In addition, where the screen on which they are displayed is a touch sensitive screen, they can be actuated using touch gestures. Also, where the device that displays them has speech recognition components, they can be actuated using speech commands.

Data store(s) have also been discussed. It will be noted they can each be broken into multiple data stores. All can be local to the systems accessing them, all can be remote, or some can be local while others are remote. All of these configurations are contemplated herein. A data store can include all types of tangible volatile and non-volatile computer-readable memory devices. It can also include computer storage media. Memory, for example, can store computer readable instructions that, when executed by a processor, cause the processor to perform any of the above-described or functions.

Also, the figures show a number of blocks with functionality ascribed to each block. It will be noted that fewer blocks can be used so the functionality is performed by fewer components. Also, more blocks can be used with the functionality distributed among more components.

Figure 9:
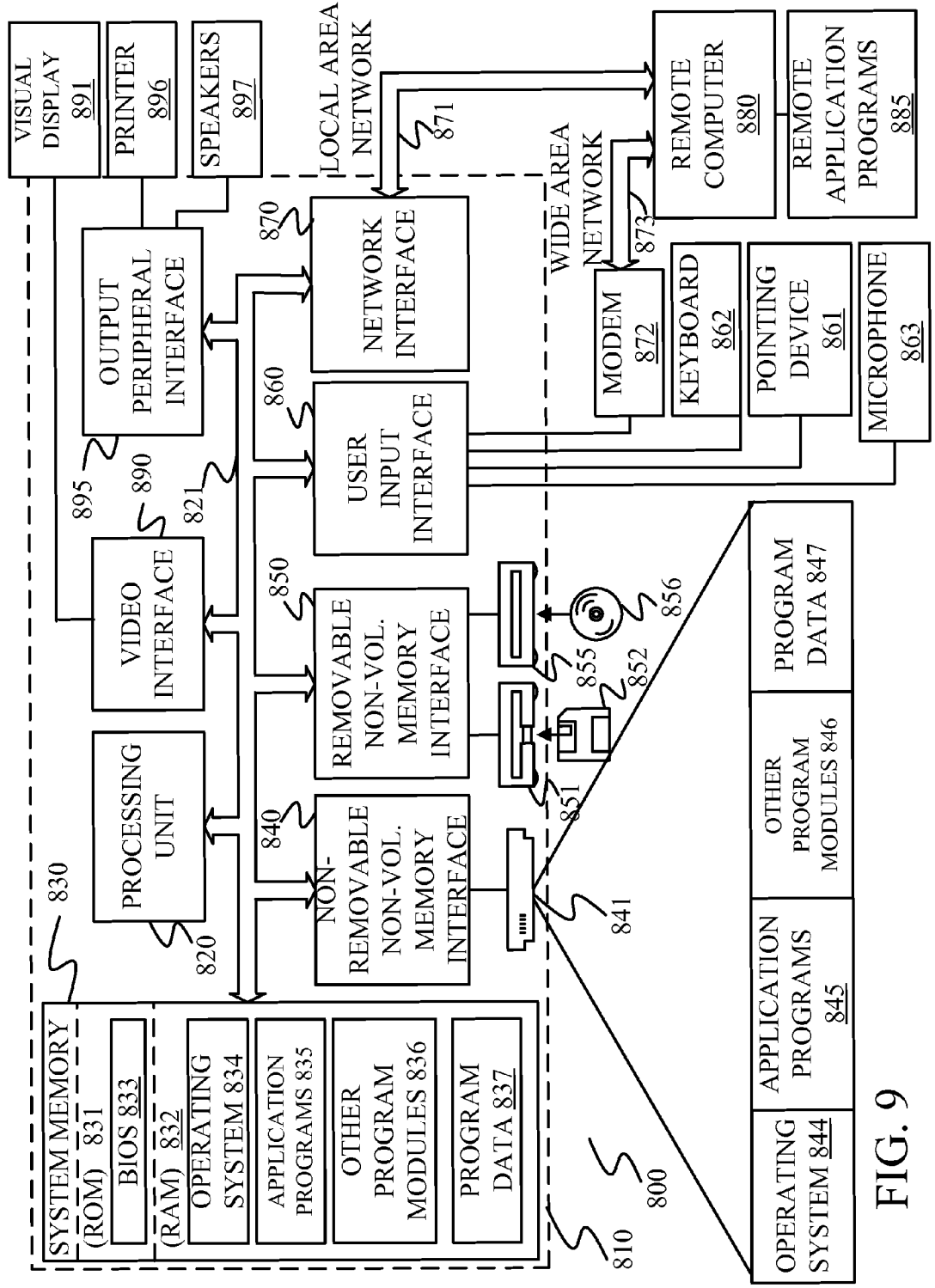
FIG. 9 is a block diagram of one example of a computing environment that can be deployed in any of the machines, systems, and/or architectures shown in previous figures.

FIG. 9 is one example of a computing environment in which elements of FIG. 4, or parts of it, (for example) can be deployed. With reference to FIG. 9, an example system for implementing some embodiments includes a general-purpose computing device in the form of a computer 810. Components of computer 810 may include, but are not limited to, a processing unit 820 (which can comprise processors from previous FIGS.), a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. Memory and programs described with respect to FIG. 4 can be deployed in corresponding portions of FIG. 9.

Computer 810 typically includes a variety of computer readable media. Computer readable media can be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media may embody computer readable instructions, data structures, program modules or other data in a transport mechanism and includes any information delivery media. The term "modulated data signal" means a signal that has one or more of its characteristics set or changed in such a manner as to encode information in the signal.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 9 illustrates operating system 834, application programs 835, other program modules 836, and program data 837.

The computer 810 may also include other removable/non-removable volatile/nonvolatile computer storage media. By way of example only, FIG. 9 illustrates a hard disk drive 841 that reads from or writes to non-removable, nonvolatile magnetic media, an optical disk drive 855, and nonvolatile optical disk 856. The hard disk drive 841 is typically connected to the system bus 821 through a non-removable memory interface such as interface 840, and optical disk drive 855 are typically connected to the system bus 821 by a removable memory interface, such as interface 850.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 9, provide storage of computer readable instructions, data structures, program modules and other data for the computer 810. In FIG. 9, for example, hard disk drive 841 is illustrated as storing operating system 844, application programs 845, other program modules 846, and program data 847. Note that these components can either be the same as or different from operating system 834, application programs 835, other program modules 836, and program data 837.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, levers, buttons, steering wheels, foot pedals, or the like. These and other input devices are often connected to the processing unit 820 through a user input interface 860 that is coupled to the system bus, but may be connected by other interface and bus structures. A visual display 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections (such as a local area network—LAN, or wide area network WAN) to one or more remote computers, such as a remote computer 880.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. In a networked environment, program modules may be stored in a remote memory storage device. FIG. 9 illustrates, for example, that remote application programs 885 can reside on remote computer 880.

It should also be noted that the different examples described herein can be combined in different ways. That is, parts of one or more examples can be combined with parts of one or more other examples. All of this is contemplated herein.

Example 1 is an agricultural planting machine comprising a trench opener configured to open a trench, and a trench depth sensing system comprising a ground-engaging component and a capacitive sensor comprising a transmitter element driven by an input signal to generate an electric field and a receiver element configured to generate an output signal based on a capacitive coupling between the transmitter and receiver elements, wherein the capacitive coupling changes based on movement of the ground-engaging component within the electric field. A trench depth calculation component is configured to generate an indication of trench depth based on the output signal.

Example 2 is the agricultural planting machine of any or all previous examples, wherein the agricultural planting machine comprises one of a box drill, an air seeder, or a row crop planter.

Example 3 is the agricultural planting machine of any or all previous examples, wherein the capacitive sensor is fixedly positioned on the row unit proximate the ground engaging component.

Example 4 is the agricultural planting machine of any or all previous examples, wherein the trench depth calculation component is configured to determine a location of the ground-engaging component relative to the capacitive sensor based on the signal, and to calculate the trench depth based on the location of the ground-engaging component relative to the capacitive sensor and a distance from the capacitive sensor to the trench opener.

Example 5 is the agricultural planting machine of any or all previous examples, wherein the ground-engaging component is configured to engage the ground adjacent the trench.

Example 6 is the agricultural planting machine of any or all previous examples, wherein the ground engaging component comprises a gauge wheel.

Example 7 is the agricultural planting machine of any or all previous examples, wherein the capacitive sensor comprises an array of capacitive sensing elements, each sensing element being configured to generate an output signal that is indicative of dielectric properties of a medium proximate the sensing element.

Example 8 is the agricultural planting machine of any or all previous examples, wherein the trench depth sensing system comprises a trench depth calculation component configured to determine the location of the ground engaging component based on a comparison of signals from the capacitive sensing elements, and to calculate the trench depth based on the determined location.

Example 9 is the agricultural planting machine of any or all previous examples, wherein each capacitive sensing element in the array comprises at least one transmitter element and at least one receiver element.

Example 10 is the agricultural planting machine of any or all previous examples, wherein each transmitter element is disposed between two receiver elements.

Example 11 is the agricultural planting machine of any or all previous examples, wherein the array comprises a first array of transmitter elements and a second array of transmitter elements, the first and second arrays having a different input signal phase.

Example 12 is the agricultural planting machine of any or all previous examples, wherein the array of capacitive sensing elements is aligned along a plane that faces the ground engaging component.

Example 13 is an agricultural planting machine comprising a trench opener configured to open a trench, and a trench depth sensing system comprising a ground-engaging component and a trench depth sensor configured to generate a signal indicative a displacement of the ground-engaging component by directly sensing a surface of the ground engaging component.

Example 14 is the agricultural planting machine of any or all previous examples, wherein the ground engaging component comprises a gauge wheel.

Example 15 is the agricultural planting machine of any or all previous examples, wherein the trench depth sensor comprises a capacitive sensor.

Example 16 is the agricultural planting machine of any or all previous examples, wherein the trench depth sensor comprises an optical sensor.

Example 17 is the agricultural planting machine of any or all previous examples, wherein the trench depth sensor comprises a microwave sensor.

Example 18 is the agricultural planting machine of any or all previous examples, wherein the trench depth sensor comprises an object detection sensor that utilizes radio waves.

Example 19 is an agricultural planting machine row unit comprising a trench opener configured to open a trench, and a trench depth sensing system comprising a capacitive sensor mounted on the trench opener. The capacitive sensor comprises an array of capacitive sensing elements, each capacitive sensing element having a transmitter element driven by an input signal to generate an electric field and a receiver element configured to generate an output signal indicative of dielectric properties of a medium proximate the sensing element. A trench depth indication component is configured to generate an indication of trench depth based on the output signals from the capacitive sensing elements.

Example 20 is the agricultural planting machine row unit of any or all previous examples, wherein the trench depth indication component is configured to determine whether each capacitive sensing element is adjacent a sidewall of the trench based on the dielectric properties indicated by the output signal generated by the capacitive sensing element.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An agricultural planting machine comprising:
a trench opener configured to open a trench; and
a trench depth sensing system comprising:
a ground-engaging component;
a capacitive sensor comprising a transmitter element driven by an input signal to generate an electric field and a receiver element at a fixed position relative to the transmitter element and configured to generate an output signal based on a capacitive coupling between the transmitter and receiver elements, wherein the capacitive coupling changes based on movement of the ground-engaging component, relative to the fixed position of the transmitter and receiver elements, within the electric field; and
a trench depth calculation component configured to generate an indication of trench depth based on the output signal.

2. The agricultural planting machine of claim 1, wherein the agricultural planting machine comprises one of a box drill, an air seeder, or a row crop planter.

3. The agricultural planting machine of claim 1, wherein the transmitter and receiver elements are fixedly positioned on a row unit frame of the agricultural planting machine, the transmitter and receiver elements being proximate the ground engaging component.

4. The agricultural planting machine of claim 3, wherein the trench depth calculation component is configured to determine a location of the ground-engaging component relative to the capacitive sensor based on the signal, and to calculate the trench depth based on the location of the ground-engaging component relative to the capacitive sensor and a distance from the capacitive sensor to the trench opener, and wherein the trench depth sensing system comprises a display configured to display an indication of the calculated trench depth.

5. The agricultural planting machine of claim 4, wherein the ground-engaging component comprises a gauge wheel configured to engage the ground adjacent the trench.

6. The agricultural planting machine of claim 1, wherein the capacitive sensor comprises an array of capacitive sensing elements, each capacitive sensing element being configured to generate an output signal that is indicative of dielectric properties of a medium proximate the sensing element.

7. The agricultural planting machine of claim 6, wherein the trench depth calculation component is configured to determine the location of the ground engaging component based on a comparison of signals from the capacitive sensing elements, and to calculate the trench depth based on the determined location.

8. The agricultural planting machine of claim 6, wherein each capacitive sensing element in the array comprises at least one transmitter element and at least one receiver element, and each transmitter element is disposed between two receiver elements.

9. The agricultural planting machine of claim 8, wherein the array comprises a first array of transmitter elements and a second array of transmitter elements, the first and second arrays having a different input signal phase.

10. The agricultural planting machine of claim 6, wherein the array of capacitive sensing elements is aligned along a plane that faces the ground engaging component.

11. An agricultural planting machine comprising:
a trench opener configured to open a trench; and
a trench depth sensing system comprising:
a ground-engaging component; and
a trench depth sensor comprising a transmitter element and a receiver element at a fixed position relative to the transmitter element, the trench depth sensor configured to generate a signal indicative a displacement of the ground-engaging component by directly sensing a surface of the ground engaging component.

12. The agricultural planting machine of claim 11, wherein the ground engaging component comprises a gauge wheel.

13. The agricultural planting machine of claim 11, wherein the trench depth sensor comprises a capacitive sensor.

14. The agricultural planting machine of claim 11, wherein the trench depth sensor comprises an optical sensor.

15. The agricultural planting machine of claim 11, wherein the trench depth sensor comprises a microwave sensor.

16. The agricultural planting machine of claim 11, wherein the trench depth sensor comprises an object detection sensor that utilizes radio waves.

17. An agricultural planting machine row unit comprising:
a trench opener configured to open a trench; and
a trench depth sensing system comprising:
a capacitive sensor mounted on the trench opener, the capacitive sensor comprising an array of capacitive sensing elements, each capacitive sensing element having a transmitter element driven by an input signal to generate an electric field and a receiver element configured to generate an output signal indicative of dielectric properties of a medium proximate the sensing element; and
a trench depth indication component configured to generate an indication of trench depth based on the output signals from the capacitive sensing elements.

18. The agricultural planting machine row unit of claim 17, wherein the trench depth indication component is configured to determine whether each capacitive sensing element is adjacent a sidewall of the trench based on the dielectric properties indicated by the output signal generated by the capacitive sensing element.

19. The agricultural planting machine row unit of claim 17, wherein the medium comprises soil, and the trench opener is configured to open the trench in the soil.

20. The agricultural planting machine row unit of claim 17, wherein the trench depth indication component comprises a display configured to display the indication of trench depth.

* * * * *